United States Patent [19]
Lee

[11] Patent Number: 5,597,454
[45] Date of Patent: Jan. 28, 1997

[54] PROCESS FOR PRODUCING UREA

[76] Inventor: Jing M. Lee, 11602 Blair Meadow, Stafford, Tex. 77477

[21] Appl. No.: 418,089

[22] Filed: Apr. 6, 1995

[51] Int. Cl.$^6$ .............................. B01D 3/00; B01D 3/38; C07C 273/16

[52] U.S. Cl. .......................... 203/49; 159/47.2; 203/27; 203/29; 203/95; 564/66; 564/71; 564/72; 564/73

[58] Field of Search ................................. 203/27, 29, 49, 203/39, 95; 159/47.2; 562/555, 554; 564/63, 66, 67, 70, 71, 72, 73

[56] References Cited

U.S. PATENT DOCUMENTS

| | | | |
|---|---|---|---|
| 3,668,250 | 6/1972 | Karafian | 260/555 A |
| 3,711,544 | 1/1973 | Summerville | 260/555 A |
| 3,886,210 | 5/1975 | Mavrovic | 260/555 A |
| 4,231,839 | 11/1980 | Barron et al. | 159/47 UA |
| 4,296,252 | 10/1981 | Mavrovic | 564/70 |
| 4,316,767 | 2/1982 | Saida et al. | 159/47.2 |
| 4,410,503 | 10/1983 | van Nassau et al. | 423/359 |
| 4,456,535 | 6/1984 | Zuidam et al. | 210/750 |
| 4,504,679 | 3/1985 | Inoue et al. | 564/72 |
| 4,539,077 | 9/1985 | Jonckers et al. | 203/49 |
| 4,552,979 | 11/1985 | Stokes | 564/69 |
| 4,801,745 | 1/1989 | Meessen et al. | 564/71 |
| 4,864,059 | 9/1989 | Fujii | 564/72 |

FOREIGN PATENT DOCUMENTS 1110280  4/1968  United Kingdom .......... C07C 127/04

OTHER PUBLICATIONS

Hydrocarbon Processing, Nov. 1977, pp. 232–233.

*Primary Examiner*—Robert J. Warden
*Assistant Examiner*—Robert Carpenter
*Attorney, Agent, or Firm*—Sroufe, Payne & Lundeen

[57] ABSTRACT

A urea production process combining lower pressure urea concentration and carbamate recovery steps into a single non-vacuum operation. Following high pressure stripping wherein a bulk of unreacted carbamate is recovered from the reaction effluent, remaining carbamate is stripped by heated air at atmospheric pressure wherein urea is concurrently concentrated without the use of vacuum evaporators. Weak carbamate solution subsequently formed is stripped of water (and residual urea is hydrolyzed) using air and steam at a medium pressure single tower hydrolyzer/stripper to obtain a concentrated carbamate stream suitable for recycle to the reactor. The process employs heat integration for enhanced energy efficiency and produces a good quality aqueous condensate suitable for direct use as boiler feed water. Thus the aqueous condensate produced requires no additional cooling and ammonia treatment. The process employs simplified and reduced process unit operation to eliminate equipment for cost reduction.

11 Claims, 1 Drawing Sheet

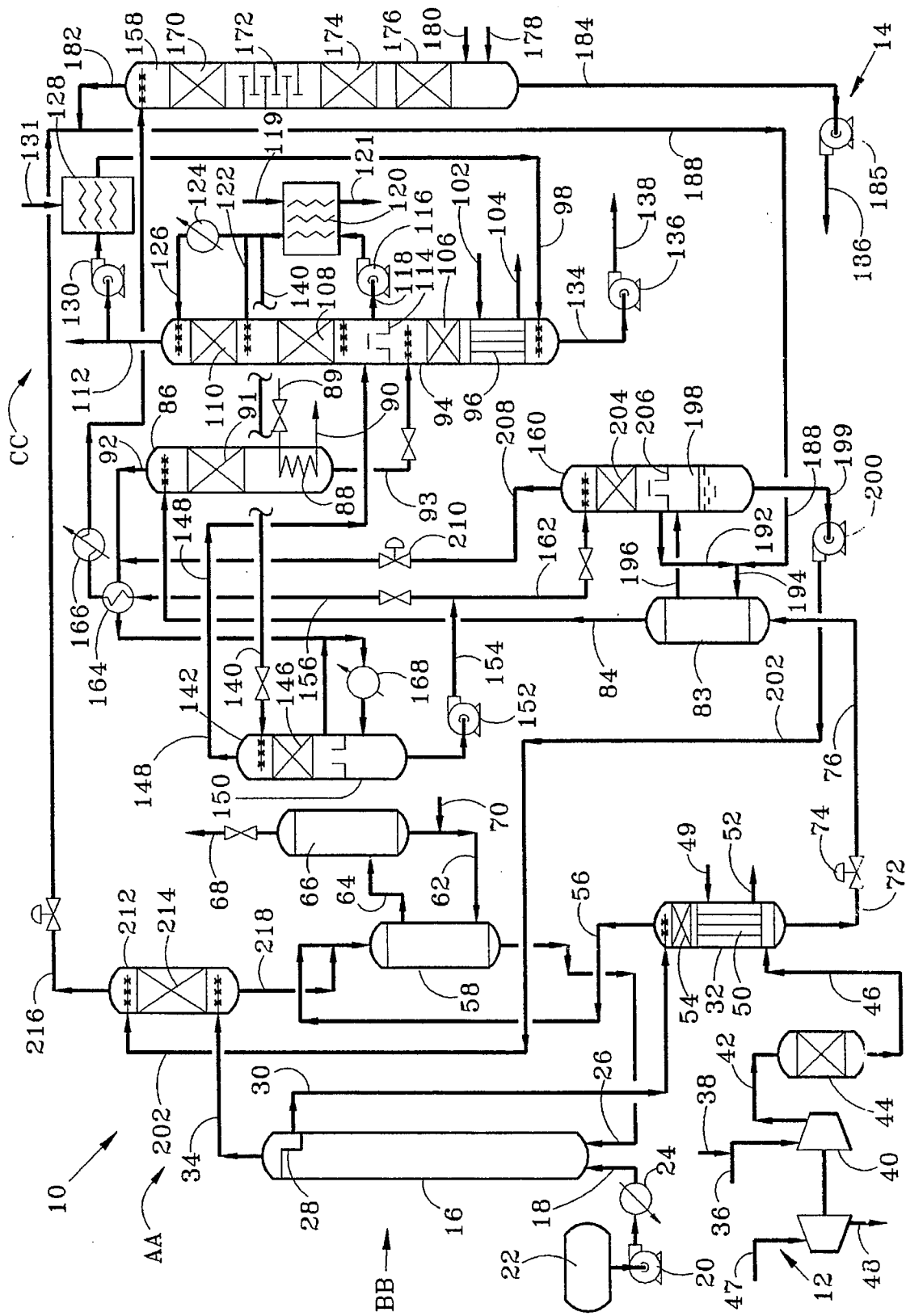

PROCESS FOR PRODUCING UREA

FIELD OF THE INVENTION

The present invention relates to a urea production process, and more particularly to a urea process combining lower pressure urea concentrating and carbamate stripping steps into a single operation.

BACKGROUND OF THE INVENTION

Urea is manufactured as the direct reaction product of ammonia and carbon dioxide at an elevated temperature and pressure. Ammonium carbamate is produced as an intermediate followed substantially simultaneously by dehydration to urea. Both reaction stages are substantially reversible depending on the equilibrium concentration of the reactants.

In the prior art, such as the well known Stamicarbon and Snamprogetti processes, urea reactor effluent containing aqueous urea solution and unreacted carbamate is subject to a series of stripping operations at high, medium and low pressures to remove residual carbamate and ammonia and $CO_2$ components. The stripped gases are then condensed back to carbamate and recycled to the reactor. Following the removal of unconverted carbamate, the urea solution is concentrated under progressively higher vacuum to evaporate the water, or by crystallization. Concentrated urea can then be prilled or granulated to form solid urea product.

Applicant is unaware of a prior art urea production process wherein the reaction effluent is stripped of carbamate and the urea solution is concentrated in a single operation carried out at a superatmospheric pressure.

SUMMARY OF THE INVENTION

A urea reactor effluent is stripped of residual carbamate and concentrated in a single operation at a pressure at or above atmospheric. The aqueous carbamate stream thus recovered is concentrated in a combined hydrolyzer/stripper column for return to the reaction cycle. Aqueous condensate removed from the hydrolyzer column has a quality suitable for use as boiler feed water without further cooling or treatment. In addition, heat of carbamate condensation (association) can be advantageously recovered.

A urea production process is provided. As a step (a), ammonia and carbamate are continuously reacted at an elevated pressure and temperature to form an aqueous effluent stream containing urea, ammonia and carbamate. As step (b), ammonia and carbamate are stripped from the effluent stream from step (a) at about the reaction pressure to form a high pressure stripper bottoms stream of enhanced urea content containing from about 15 to about 30 percent by weight ammonium carbamate. As step (c), the high pressure bottoms steam from step (b) is heated at a relatively lower superatmospheric pressure to drive off water and ammonium carbamate vapor to form a low pressure stripper overhead stream containing at least about 30 weight percent water vapor, and form a low pressure stripper bottoms stream having a urea content of at least about 80 weight percent and an ammonium carbamate concentration less than about 2 weight percent. As step (d), the low pressure stripper bottoms stream from step (c) is heated and contacted with an inert gas, such as air, for example, to form a concentrated urea product stream suitable for prilling or granulation. As step (e), the low pressure stripper overhead stream from step (c) is concentrated to form an aqueous stream of at least 70 weight percent ammonium carbamate for recycle to the reaction step (a).

In a preferred embodiment, the concentration step (e) comprises the steps of: (1) cooling the overhead stream from step (c) to form a condensate stream; (2) contacting remaining vapor from step (e)(1) with an aqueous stream to form a vapor stream of reduced ammonia and carbamate content; (3) collecting and feeding at least a major portion of the liquid streams from steps (e)(1) and (e)(2) to a high pressure hydrolyzer/stripper unit for contacting with stripping steam to form the concentrated ammonium carbamate recycle stream overhead and a bottoms condensate stream essentially free of ammonia and carbamate.

A major portion of the heating in step (c) is preferably supplied by the step of (f) at least partially condensing the overhead recycle carbamate stream from step (e)(3) in indirect heat exchange against the high pressure stripper bottoms stream.

The process preferably comprises the step of (g) contacting remaining vapor from the partial condensation step (f) with a minor portion of the collected streams from step (e)(3) and combining the resultant liquid with the condensate from step (f) to form the ammonium carbamate recycle stream. The heating and contacting step (d) preferably comprises the steps of: (1) heating air; (2) introducing the heated air at a bottom of a urea concentrating zone of a urea concentrator column; (3) introducing the low pressure stripper bottoms stream from step (c) to a top of the urea concentrating zone to countercurrently contact the heated air; (4) introducing a mixture of air and steam from the top of the urea concentrating zone into a lower end of a cooling zone disposed above the urea concentrating zone in the urea concentrator column; (5) introducing condensate to an upper end of the cooling zone to countercurrently contact the air/steam mixture, condense steam from the mixture and cool the air; (6) passing the cooled air from the upper end of the cooling zone into a vent line; (7) recirculating air from the vent line in step (d)(6) to the heating step (d)(1); (8) collecting and cooling condensate from lower end of the cooling zone; (9) recirculating the cooled condensate from step (d)(8) to the introduction step (d)(5).

The process preferably further includes the steps of: (h) introducing the vapor stream from step (e)(2) into the urea concentrator column adjacent the lower end of the cooling zone; and (i) supplying a portion of the cooled condensate from step (d)(8) as the aqueous stream to the contacting step (e)(2).

BRIEF DESCRIPTION OF THE DRAWING

The FIGURE is a schematic flow diagram of the urea production process of the present invention.

DETAILED DESCRIPTION OF THE INVENTION

The steps of stripping ammonium carbamate and concentrating urea are combined in single operation at a superatmospheric pressure to eliminate the need for vacuum concentrators and associated equipment. A weak carbamate solution thus obtained is then concentrated for recycle to the reaction stage. Aqueous condensate recovered can be sent directly to steam generation to obviate the need for a condensate cooler. The heat of carbamate condensation can be recovered as low pressure steam for use in the process as a heat source and stripping vapor.

Referring to the FIGURE, a urea production process AA of the present invention comprises a high pressure urea synthesis cycle BB and a combined, low pressure carbamate stripping and urea concentrating cycle CC. In the synthesis cycle BB, urea is synthesized in a reactor 16 and a portion of the unreacted carbamate is recovered without depressurization for recycle thereto. In the lower pressure carbamate stripping and urea concentrating cycle CC, the remaining carbamate is recovered as a dilute aqueous stream. Concurrently, water is removed from the urea product and the dilute carbamate stream is concentrated for recycle to the synthesis cycle BB. As used herein, ammonium carbamate is referred to as "carbamate" and "carbamate vapor" can include ammonia and carbon dioxide dissociated components.

In the high pressure synthesis cycle BB, a liquid ammonia makeup stream is introduced to a lower end of the urea synthesis reactor 16 via line 18. The ammonia make-up stream 18 can be pumped by pump 20 from a storage tank 22 and preheated in a heater 24 to a temperature on the order of 110° C. using low pressure steam as a heating medium. In the reactor 16, the make-up ammonia stream 18 is mixed with a recycle carbamate stream introduced via line 26. Additional ammonium carbamate is produced and a portion thereof is condensed into urea and water. A reaction effluent stream comprising aqueous urea, unreacted carbamate (20 to about 30 percent of the total weight), and ammonia preferably overflows into a withdrawal pan 28 disposed at an upper end of the reactor 16 and is passed via line 30 to a high pressure carbamate stripping column 32. A vapor stream comprising non-condensable gas such as passivating oxygen or air and some carbamate vapor are withdrawn overhead from the reactor 16 via line 34.

While several different arrangements of the synthesis cycle AA can be used including those characterized by the Snamprogetti and Stamicarbon processes, the reactor 16 is preferably operated similarly to the Snamprogetti process with a molar ratio of ammonia to carbon dioxide of about 3.5–3.8:1 $NH_3:CO_2$, a temperature of about 190° C., a pressure of about 165 to 170 kg/cm$^2$ and a $H_2O$ to $CO_2$ molar ratio of about 0.45 to 0.55 of $H_2O:CO_2$. Urea conversion per pass is typically 64 to 69 percent based on the total $CO_2$ introduced.

The synthesis cycle BB includes the high pressure stripper 32 operating at about the pressure of reactor 16 to recover a portion of the unreacted carbamate, typically 60–85 percent thereof from the reaction effluent stream 30. In the high pressure stripper 32, carbamate is substantially dissociated into ammonia and $CO_2$ and then preferably stripped using a make-up $CO_2$ stream as a stripping fluid. As is well known, other stripping fluids can be used such as, for example, make-up ammonia utilized in the Toyo process. Typically, a raw $CO_2$ stream introduced via line 36 is combined with a corrosion passivating amount of an oxygen-containing stream introduced via line 38 and compressed by a $CO_2$ compressor 40. A compressed $CO_2$ stream is directed via line 42 to a hydrogen combustor 44 wherein hydrogen is burned. A hydrogen-lean $CO_2$ stream is removed via line 46 and directed to the high pressure carbamate stripper 32 as the stripping fluid mentioned above. The compressor 40 can have a steam drive with higher pressure steam introduced thereto via line 47. Expanded steam and condensate are removed via line 48.

The heat of carbamate dissociation is typically provided by the condensation of steam fed via line 49 to a heating zone 50. Condensed steam is then withdrawn from the heating zone 50 via line 52. The heating zone 50 generally comprises a falling film heat exchanger. Urea carried upward by the rising $CO_2$ and carbamate vapor is substantially absorbed therefrom by contact with the reaction effluent stream 30 in an absorption zone 54.

A vapor stream substantially comprising $CO_2$ and carbamate is removed overhead via line 56 combined with a concentrated carbamate stream 218 from the urea concentrating cycle CC and scrubber 212. Carbamate is condensed in condenser 58 and recycled to the reactor 16 via line 26. Heat of carbamate condensation (and formation) is recovered to boiler feed water (BFW) introduced to a condenser shell side via line 62. Boiler feed water (BFW) and steam are withdrawn via line 64 and steam separated in a steam drum 66 to produce steam having a pressure of about 4–5 kg/cm$^2$ which can be withdrawn via line 68 for further use in the process 10. Make-up BFW is introduced via line 70.

An aqueous urea stream comprising less than 30 percent by weight carbamate, preferably less than 22 percent by weight, is withdrawn from the high pressure stripper 32 via line 72, adiabatically expanded to a pressure of about 1.1 kg/cm$^2$ through let-down valve 74 and directed to the lower pressure carbamate stripping and urea concentration cycle CC via line 76. The lower pressure cycle CC includes preliminary and primary carbamate stripping and urea concentrating stages carried out at about atmospheric pressure, and a urea hydrolyzing and carbamate concentrating stage. The concentrating stage is operated at a high enough pressure so that the heat released and recovered from carbamate condensation (association) is sufficiently great to allow it to be used as a source of heat for carbamate dissociation in the preliminary low pressure stripping stage. As a result, the carbamate concentrating stage preferably has a pressure above about 20 kg/cm$^2$.

The low pressure aqueous urea and carbamate stream 76 is directed to a tube side of a low pressure carbamate condenser 83 as a cooling medium for condensation of a concentrated carbamate vapor stream recovered from the carbamate concentrating stage. Warmed to a temperature on the order of 110° C., aqueous urea and carbamate stream 84 is introduced to the preliminary low pressure stripping stage. The stripping stage comprises a stripping column 86 having a lower dissociation zone 88 wherein heat supplied by condensing steam dissociates carbamate into ammonia and $CO_2$. The steam which is supplied via line 89 can be obtained from the steam drum 66, for example. Steam condensate is removed via line 90. Carbamate vapor rising from the dissociation zone 88 strips carbamate and water from down-flowing aqueous urea and carbamate in an upper absorption zone 91 comprising vapor-liquid contacting elements. Concurrently, the aqueous stream absorbs urea from the vapor. A vapor stream of reduced carbamate content is removed overhead from the preliminary stripper via line 92 for treatment in the carbamate concentration stage. A urea bottoms stream concentrated to about 80–90 percent by weight urea is directed to the primary urea concentrating and carbamate stripping stage via line 93.

The primary urea concentrating and carbamate stripping stage comprises a primary stripping column 94 operating at a pressure slightly above atmospheric and employing heated air as a stripping fluid. The primary stripping column 94 includes a lower heating zone 96 wherein urea is heated by condensing steam and concurrently stripped by heated air as the inert gas introduced via line 98. The heated zone 96 preferably comprises a falling film heat exchanger wherein steam is introduced via line 102 and steam condensate is removed via line 104. Steam is preferably supplied to the heat exchanger 96 from the steam drum 66.

Gas rising from heating zone 96 substantially comprising moist air and a small quantity of carbamate and urea passes through a urea absorption zone 106 comprising vapor-liquid contact elements wherein urea carried by the up-flowing stripping air is substantially absorbed therefrom into concentrated down-flowing urea solution. A urea-lean air stream comprising water and carbamate vapor is thermally quenched and the aqueous components are substantially completely absorbed therefrom in lower and upper quench/absorption zones 108, 110 disposed in an upper portion of the column 94.

In the lower absorption zone 108, up-flowing air is contacted with a dilute aqueous carbamate absorbent having a temperature on the order of 37° C. In the upper absorption zone 110, air passing from the lower zone 108 is contacted with a dilute aqueous carbamate absorbent chilled to a temperature on the order of 15° C. An essentially carbamate-free air stream chilled to a temperature of about 15° C. and having a low moisture content is withdrawn overhead from the column 94 via line 112.

A warm, dilute carbamate stream having a temperature on the order of 80° C. and accumulating on a withdrawal tray 114 is pumped by pump 116 therefrom via line 118 for use as cooling absorbent in the quench/absorption zones 108, 110. The warm carbamate stream 118 is cooled to a temperature of about 37° C. by heat exchange against cooling water supplied via line 119 in a cooler 120. Discharged cooling water is withdrawn via line 121. The cooler 120 preferably comprises a fin-plate exchanger. A portion of the cool, dilute carbamate absorbent is introduced to the lower quench zone 108 via line 122. Another portion of the cool, dilute carbamate absorbent is further cooled by an exchange of heat against liquid ammonia or other refrigerant in a chiller 124 and introduced to the upper quench zone 110 via line 126.

Chilled and dried air is taken from vent line 112 and circulated to a heater 128 by a blower 130. The air heater 128 heats the circulating air to a temperature of about 140° C. by heat exchange against steam introduced via line 131. A dry, heated air stripping stream is circulated to the column 94 via line 98 as previously mentioned. A concentrated urea product stream is removed from the column 94 as a bottoms product via line 134. The urea bottoms stream 134 is pumped by pump 136 via line 138 to a finishing stage (not shown) for prilling, granulation, or the like. The concentration of urea in stream 138 is generally appropriate for the type of finishing desired, such as, for example, 99.7 percent urea for prilling, or a slightly lower concentration for granulation.

A portion of the dilute aqueous carbamate recovered from the quench zones 108, 110 is withdrawn via line 140 for concentration in the carbamate concentrating stage. The carbamate concentrating stage comprises a low pressure carbamate condenser column 142 and a medium pressure hydrolyzer/carbamate stripper column 158.

The weak carbamate vapor stream 92 is precooled in the heat exchanger 164, cooled to a temperature of about 50° C. by heat exchange against cooling water in a cooler 168, fed to the low pressure carbamate condenser column 142, and quenched in a quench zone 146 by direct contact with the cool, process condensate stream 140 taken from the primary stripping column 94. A non-condensable gas (e.g. air) is removed overhead from the carbamate condenser column 142 and recycled to the lower quench zone 108 of the primary stripper 94 via line 148. Dilute aqueous carbamate cooled to a temperature of about 50° C. by the quench is accumulated in a lower vapor-liquid separation zone 150.

The cool, dilute, low pressure carbamate stream 150 is pumped by pump 152 primarily to the medium pressure hydrolyzer/carbamate condenser column 158 via line 154. A major portion of the dilute carbamate stream 154 is directed via line 156 to the medium pressure urea hydrolyzer/carbamate stripper column 158. The major dilute carbamate portion in line 156 is heated to a temperature on the order of 130° C. prior to introduction to the hydrolyzer/stripper 158. The dilute carbamate stream in line 156 is preferably preheated in a heat exchanger 164 by heat exchange against the weak carbamate vapor stream 92 from the low pressure stripper 86 and further heated by heat exchange against steam in a heater 166.

In the hydrolyzer/stripper column 158, the dilute carbamate aqueous feed stream 156 is heated and contacted in a series of vapor-liquid contacting zones 170, 172, 174, 176 by stripping air and steam introduced via lines 178, 180. The contacting zones 170, 172, 174, 176 can comprises either vapor-liquid packing elements or trays. Any residual urea present in the feed stream 156 is thus hydrolyzed to carbamate. Residual carbamate is, in turn, dissociated and stripped. A concentrated carbamate vapor stream comprising 85 percent by weight carbamate or more is taken overhead from the hydrolyzer/stripper 158 via line 182. A purified water stream comprising less than 5 ppmw combined ammonia and urea is withdrawn as a bottoms stream from the hydrolyzer/stripper 158 via line 184. The purified aqueous condensate stream 184 has a quality suitable for use as boiler feed water and is pumped by pump 185 via line 186 to steam generation (not shown). Additional details regarding the operation of the hydrolyzer/stripper column 158 can be found in my U.S. Ser. No. 08/238,255, filed May 4, 1994, now abandoned, which disclosure is hereby incorporated herein by reference.

The concentrated carbamate vapor stream 182 is combined with residual vapor obtained from the synthesis cycle BB and directed to a shell side of the carbamate condenser 83 via line 188. The concentrated carbamate vapor stream 188 is combined with a dilute aqueous carbamate stream withdrawn from the medium pressure carbamate absorption and vapor-liquid separation column 160 via line 192 to facilitate carbamate condensation in the condenser 83. A combined two phase carbamate stream is introduced to the condenser 83 via line 194. The concentrated carbamate stream 194 is substantially condensed (associated) into a concentrated liquid phase and heat of association is recovered into the tube side low pressure aqueous urea and carbamate stream 76 for heating thereof prior to introduction to the low pressure stripper 86, as mentioned above.

A substantially condensed concentrated carbamate stream having a temperature of about 120° C. is withdrawn from the condenser 83 via line 196 and directed to a vapor-liquid separation zone 198 of the carbamate absorption and vapor-liquid separation column 160. In the vapor-liquid separation zone 198, carbamate condensate comprising about 75 percent by weight carbamate is separated from uncondensed vapor (e.g. passivating oxygen and carbamate). The concentrated carbamate condensate is withdrawn as a bottoms stream from the column 160 via line 199 and recycled by pump 200 to the urea synthesis cycle 12 via line 202. The remaining minor portion of dilute aqueous carbamate is directed as an absorbent to a medium pressure carbamate absorption and vapor-liquid separation column 160 via line 162. Vapor flowing up the column 160 is contacted by the dilute carbamate in a carbamate absorption zone 204 to absorb additional carbamate from the uncondensed vapor. A resulting aqueous carbamate stream accumulating on a withdrawal tray 206 is withdrawn therefrom via line 192 for combination with the concentrated carbamate vapor stream 188 and facilitation of carbamate condensation in the condenser 83 as mentioned above. Vapor obtained from the absorption zone 204 is withdrawn overhead from the column 160 via line 208, adiabatically expanded via let-down valve 210 and preferably combined with the weak carbamate vapor stream 92 obtained from the low pressure stripper 86 for feed to the low pressure column 142.

The concentrated carbamate stream 202 recycled to the synthesis cycle 12 is used as an absorbent for absorbing carbamate vapor from the reactor vapor stream 34 in a high pressure scrubber 212. The scrubber 212 comprises an absorption zone 214 comprising vapor-liquid contacting elements wherein carbamate and any residual urea in the up-flowing vapor 34 are absorbed therefrom into the down-flowing absorbent. A substantially carbamate-lean vapor stream comprising primarily inert gases is preferably directed via line 216 for combination with the concentrated carbamate vapor stream 182 from the hydrolyzer/stripper 158. A concentrated carbamate recycle stream is directed preferably by gravity feed from the scrubber 212 to the high pressure condenser 58 via line 218. The liquid carbamate stream 218 is combined with the $CO_2$ and carbamate vapor stream 56 obtained from the high pressure stripper 32 as mentioned above. The condensed carbamate stream thus formed contains make-up $CO_2$ and is recycled to the reactor 16 via line 26 as mentioned previously.

EXAMPLE

The urea production process of the present invention (as seen in the FIGURE) is simulated by computer algorithm to determine stream condition and composition of several of the major streams involved. Reactor 16 operating conditions are presented in Table 1. Results are presented in Table 2.

TABLE 1

| Item | Parameter |
| --- | --- |
| Reactor pressure (kg/cm$^2$) | 165 |
| Reactor temperature (°C.) | 188–190 |
| Reactor ratio NH$_3$/CO$_2$ | 3.5 |
| Reactor ratio H$_2$O/CO$_2$ | 0.5 |
| Reactor conversion (%) | 65 |
| Stripping gas in the high pressure stripper 32 | Make-up CO$_2$ |

TABLE 2

| Stream | Temp. (°C.) | Press (kg/cm$_2$) | Composition (wt %) | | | | |
| --- | --- | --- | --- | --- | --- | --- | --- |
| | | | Urea | NH$_3$ | CO$_2$ | H$_2$O | Inerts |
| Make-up NH$_3$ 18 | 110 | 165 | — | 100.0 | — | — | — |
| Recycle carbamate to reactor 26 | 172 | 165 | 0.02 | 46.15 | 40.72 | 9.17 | 3.94 |
| Reactor effluent to HP stripper 30 | 188 | 162 | 34.69 | 33.27 | 13.70 | 18.34 | — |
| CO$_2$ to HP stripper 46 | 150 | 168 | — | — | 94.10 | 0.45 | 5.45 |
| HP stripper bottoms 72 | 170 | 162 | 55.22 | 10.22 | 11.30 | 23.26 | — |
| LP stripper bottoms 93 | 120 | 1.12 | 85.00 | 0.06 | 0.03 | 14.91 | — |
| LP stripper overhead 92 | 100 | 1.1 | — | 29.08 | 32.23 | 38.69 | — |
| Urea | 140 | 1.1 | 99.70 | — | — | 0.30 | — |
| concentrator bottoms 134 Weak carbamate to hydrolyzer 154 | 45 | 1.1 | 0.37 | 23.28 | 25.08 | 51.54 | — |
| Hydrolyzer overhead 182 | 140 | 25 | — | 41.13 | 45.50 | 10.00 | 3.37 |
| Conc. carbamate to HP scrubber 202 | 120 | 25 | 0.11 | 36.64 | 40.34 | 22.91 | — |

The present urea production process is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

I claim:

1. A urea production process, comprising the steps of:
   (a) continuously reacting ammonia and carbamate at an elevated pressure and temperature to form an aqueous effluent stream containing urea, ammonia and ammonium carbamate;
   (b) stripping ammonia and carbamate from the effluent stream from step (a) at about the reaction pressure to form a high pressure stripper bottoms stream of enhanced urea content containing from about 15 to about 30 percent by weight ammonium carbamate;
   (c) heating and letting down the high pressure bottoms stream from step (b) to a relatively lower superatmospheric pressure to drive off water and ammonium carbamate vapor to form a low pressure stripper overhead stream containing at least about 30 weight percent water, and to form a low pressure stripper bottoms stream having a urea content of at least about 80 weight percent and an ammonium carbamate concentration less than about 2 weight percent;
   (d) heating and contacting the low pressure stripper bottoms stream from step (c) with an inert gas to form a urea product stream having a concentration suitable for prilling or granulation;
   (e) concentrating the low pressure stripper overhead stream from step (c) to form an aqueous stream of at least 70 weight percent ammonium carbamate; and
   (f) recycling said aqueous stream from step (e) to the reaction step (a).

2. The process of claim 1, wherein the concentrating step (e) comprises the steps of:
   (1) cooling the overhead stream from step (c) to form a condensate stream;
   (2) contacting remaining vapor from step (e)(1) with an aqueous stream to form a vapor stream of reduced ammonia and carbamate content;
   (3) collecting and feeding at least a major portion of the liquid streams from steps (e)(1) and (e)(2) to a high pressure hydrolyzer/stripper unit for contacting with steam to form the concentrated ammonium carbamate recycle stream overhead and a bottoms condensate stream essentially free of ammonia and carbamate.

3. The process of claim 2, wherein a major portion of the heating in step (c) is supplied by the further step of (g) at least partially condensing the overhead recycle carbamate stream from step (e)(3) in indirect heat exchange with the high pressure stripper bottoms stream.

4. The process of claim 3, further comprising the step of (h) contacting remaining vapor from the partial condensation step (g) with a minor portion of the collected streams from step (e)(3) and combining the resultant liquid with the condensate from step (g) to form the ammonium carbamate recycle stream.

5. The process of claim 4, wherein the heating and contacting step (d) comprises the steps of:

(1) heating air;

(2) introducing the heated air at a bottom of a urea concentrating zone of a urea concentrator column;

(3) introducing the low pressure stripper bottoms stream from step (c) to a top of the urea concentrating zone to countercurrently contact the heated air;

(4) introducing a mixture of air and steam from the top of the urea concentrating zone into a lower end of a cooling zone disposed above the urea concentrating zone in the urea concentrator column;

(5) introducing condensate to an upper end of the cooling zone to countercurrently contact the air/steam mixture, to condense steam from the mixture and to cool the air;

(6) passing the cooled air from the upper end of the cooling zone into a vent line;

(7) recirculating air from the vent line in step (d)(6) to the heating step (d)(1);

(8) collecting and cooling condensate from the lower end of the cooling zone;

(9) recirculating the cooled condensate from step (d)(8) to the introduction step (d)(5).

6. The process of claim 5, further comprising the steps of:

(i) introducing the vapor stream from step (e)(2) into the urea concentrator column adjacent the lower end of the cooling zone; and (j) supplying a portion of the cooled condensate from step (d)(8) as the aqueous stream to the contacting step (e)(2).

7. The process of claim 2, comprising concurrently hydrolyzing urea, stripping ammonia and $CO_2$, and forming the concentrated ammonium carbamate recycle stream from the carbamate solution collected in step (e)(3) in the high-pressure hydrolyzer/stripper unit, wherein the high-pressure hydrolyzer/stripper comprises a single column.

8. The process of claim 1, wherein the relatively lower superatmospheric pressure of step (c) is about 1.1 $kg/cm^2$.

9. The process of claim 1, wherein the stripping step (b) is at a pressure of about 165–170 $kg/cm^2$.

10. The process of claim 1, further comprising condensing the ammonia and ammonium carbamate stripped in step (b), recycling the condensed ammonia and carbamate to the reaction step (a) and supplying a makeup ammonia stream to the reaction step (a).

11. The process of claim 10, wherein the makeup ammonia is supplied by pumping liquid ammonia through a heater, and introducing the heated ammonia to a urea reactor for the reaction step (a).

* * * * *